(12) United States Patent
Sartorio et al.

(10) Patent No.: US 6,319,238 B1
(45) Date of Patent: Nov. 20, 2001

(54) ABSORBENT INTERLABIAL ARTICLE

(75) Inventors: Anthony T. Sartorio, Skillman, NJ (US); Christopher McDonald Holliday, Levittown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/310,296

(22) Filed: May 12, 1999

(51) Int. Cl.$^7$ ............................. A61F 5/44; A61F 13/20
(52) U.S. Cl. ................... 604/330; 604/346; 604/385.17
(58) Field of Search ................... 604/330, 331, 604/346, 358, 387, 385.17, 1, 2, 3

(56) References Cited

U.S. PATENT DOCUMENTS

| | | | |
|---|---|---|---|
| 1,537,992 | * 5/1925 | Gearon | 128/285 |
| 2,499,414 | * 3/1950 | Rabell | 128/285 |
| 2,917,049 | * 12/1959 | Delaney | 128/285 |
| 3,079,921 | * 3/1963 | Brecht et al. | 128/285 |
| 3,397,695 | * 8/1968 | Voss | 128/285 |
| 3,528,422 | 9/1970 | Hodas . | |
| 3,762,414 | * 10/1973 | Burnhill | 128/285 |
| 3,965,905 | * 6/1976 | Schoenholz et al. | 128/285 |
| 3,983,873 | 10/1976 | Hirschman . | |
| 4,175,561 | * 11/1979 | Hirschman | 128/296 |
| 4,433,972 | 2/1984 | Malfitano . | |
| 4,490,147 | 12/1984 | Pierce et al. . | |
| 4,595,392 | 6/1986 | Johnson et al. . | |
| 5,057,096 | * 10/1991 | Faglione | 604/385.1 |
| 5,484,429 | 1/1996 | Vukos et al. . | |
| 5,520,675 | 5/1996 | Knox-Sigh . | |
| 5,584,827 | * 12/1996 | Korteweg et al. | 604/369 |
| 5,762,644 | * 6/1998 | Osborn, III et al. | 604/385.1 |
| 5,846,230 | 12/1998 | Osborn, III et al. . | |
| 5,891,126 | * 4/1999 | Osborn, III et al. | 604/385.1 |
| 5,895,381 | * 4/1999 | Osborn, III | 604/385.1 |
| 5,968,026 | * 10/1999 | Osborn, III et al. | 604/378 |
| 6,080,908 | * 6/2000 | Guarracino et al. | 604/359 |

FOREIGN PATENT DOCUMENTS

| | | |
|---|---|---|
| 2059096 | 7/1993 | (CA) . |
| 2 319 186 A | 5/1998 | (GB) . |
| WO 96/07379 | 3/1996 | (WO) . |
| WO 98 22059 A | 5/1998 | (WO) . |

* cited by examiner

Primary Examiner—John G. Weiss
Assistant Examiner—Paul Shanoski

(57) ABSTRACT

The present invention relates to an absorbent article designed and configured to fit between the labia. The article employs a plurality of stacked, flexible elements and provides improved fit and article retention, improved collection of bodily fluids and solids typically left unabsorbed by conventional interlabial products, ability to deliver various additives such as medicaments to the tissue surrounding the labia, and an adjustable placement depth to meet consumers varying physical and psychological needs.

3 Claims, 3 Drawing Sheets

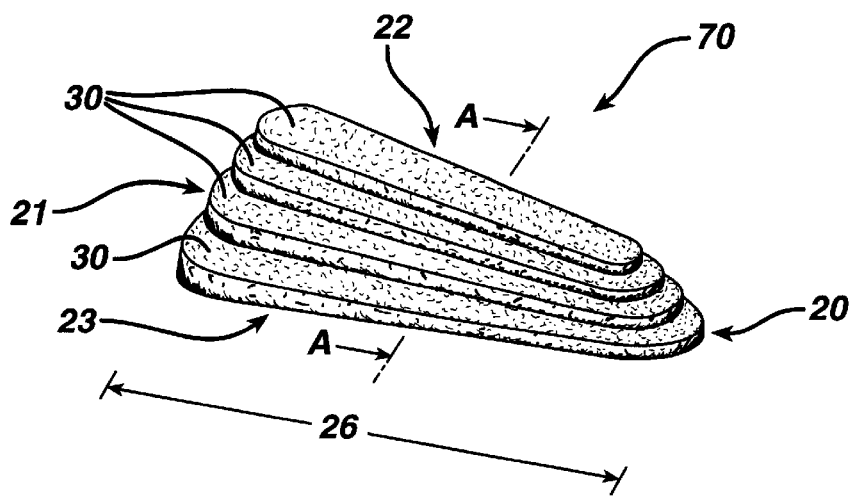
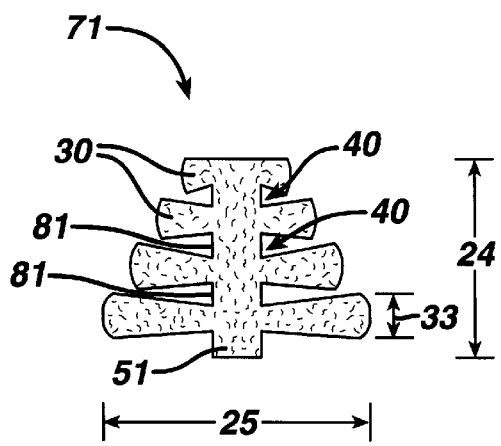
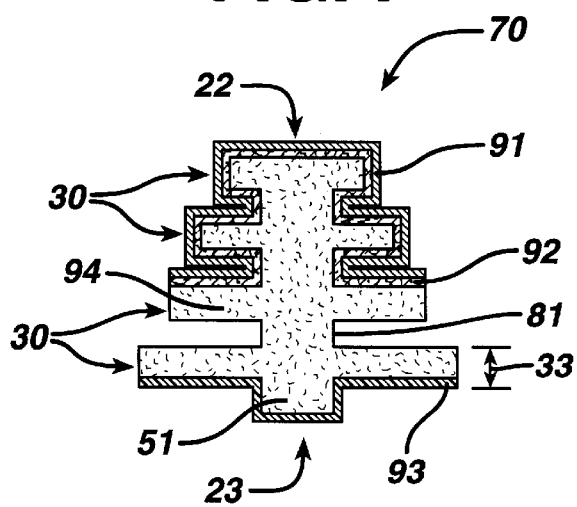

ABSORBENT INTERLABIAL ARTICLE

FIELD OF THE INVENTION

The present invention relates to an absorbent interlabial article with improved fit and comfort. The article is useful in the management of bodily fluids including but not limited to vaginal discharge, urethral discharge, and perspiration generated by glands in the perineum.

BACKGROUND OF THE INVENTION

Insertion of a fluid management article between the labia has been known for some time. A key property of an interlabial article is that it remain where inserted, thereby providing the user with the most efficient performance as well as reduced likelihood of discomfort due to distortion and chaffing. Unlike tampons that are securely positioned within the vaginal canal or sanitary napkins that are attached to a user's undergarments, known interlabial articles rely on frictional forces, normal forces, or humidity for retention within the labia.

For example, Johnson et al., U.S. Pat. No. 4,595,392, and Vukos et al., U.S. Pat. No. 5,484,429, disclose typical interlabial pads with substantially smooth outer surfaces that come into contact with the labia minora and/or majora. The smooth surfaces on each side of the pads represent single contact points. With such continuous surfaces, the effort required to remove or inadvertently dislodge a pad is substantially equal to the effort required to insert the pad. This can necessitate a compromise between placement retention properties and user-acceptable insertion properties when designing the article.

Azzali et al., PCT Application No. WO 96/07379, relies on the presence of humidity to aid in the retention of the sanitary pad. There are, however, two shortcomings of this method. First, retention is hindered if there is a lack of humidity. Second, if materials are chosen to draw moisture aggressively from the surroundings to create a seal, use of the article could result in over-drying or irritation.

Interlabial articles that are not retained where inserted have an increased potential for leakage and discomfort. Interlabial articles tend to be relatively small compared to sanitary napkins, and therefore must capture discharged fluid directly as it exits the vaginal or urethral openings. If an interlabial article's initial position is altered, fluid can travel around the article and stain the user's body or undergarments.

In addition to the need for an interabial article with improved fit and comfort is the need for an interlabial article that accounts for differences in anatomy and personal preference.

The present invention provides an interlabial article having improved fit, comfort, and fluid management characteristics through the incorporation of a plurality of stacked, flexible elements. The unique design of the present interlabial article provides several advantages over interlabial articles known in the art. One advantage is that the stacked, flexible elements provide multiple labia contacting surfaces. These multiple contacting surfaces and the channels between them improve article retention between the labia. The multiple contacting surfaces also allow the user to adjust the placement of the article between the labia. A user can adjust the depth of insertion depending on her individual body shape and size, as well as personal comfort level, without compromising retention of the article during use. A single user can also employ alternative placement positions during a time interval when more than one article is used, such as throughout a menstrual period.

The interlabial article may also preferably comprise channels to provide a reservoir for holding and delivering various additives to or through tissue in the perineum. Such channels can also provide a means for collecting clots, viscous fluids, and solids associated with vaginal discharges. The channels can provide a means for collecting various fluid and tissue samples for diagnostic analysis by medical practitioners.

SUMMARY OF THE INVENTION

The present invention provides an absorbent interlabial article sized and configured to fit between a user's labia having a body-facing side and an opposing side, comprising a plurality of stacked, flexible elements, wherein at least one of the flexible elements comprises absorbent material.

BRIEF DESCRIPTION OF THE DRAWINGS

FIG. 5 is a perspective view of an article according to the present invention having an anterior end height that is less than a posterior end height.

FIG. 6 is an end view of an article according to the present invention, comprising core elements positioned between adjacent flexible elements and an insertion aid extending from the opposing side of the article.

FIG. 7 is a cross-sectional view of an article according to the invention, comprising a liquid permeable cover, a transfer layer positioned underneath the liquid permeable cover, and a liquid impermeable backsheet.

DETAILED DESCRIPTION OF THE INVENTION

The absorbent interlabial article of the present invention is designed to stay in place during use and be comfortable and non-irritating to wear. The article effectively and efficiently absorbs liquid discharges such as those that emanate from the vagina before, during and between menstrual periods, the urethral meatus and the sweat glands. Although the article is intended to fit primarily between the labia, the article can employ optional design features that have both interlabial and extralabial residence when properly inserted.

Figure 1:
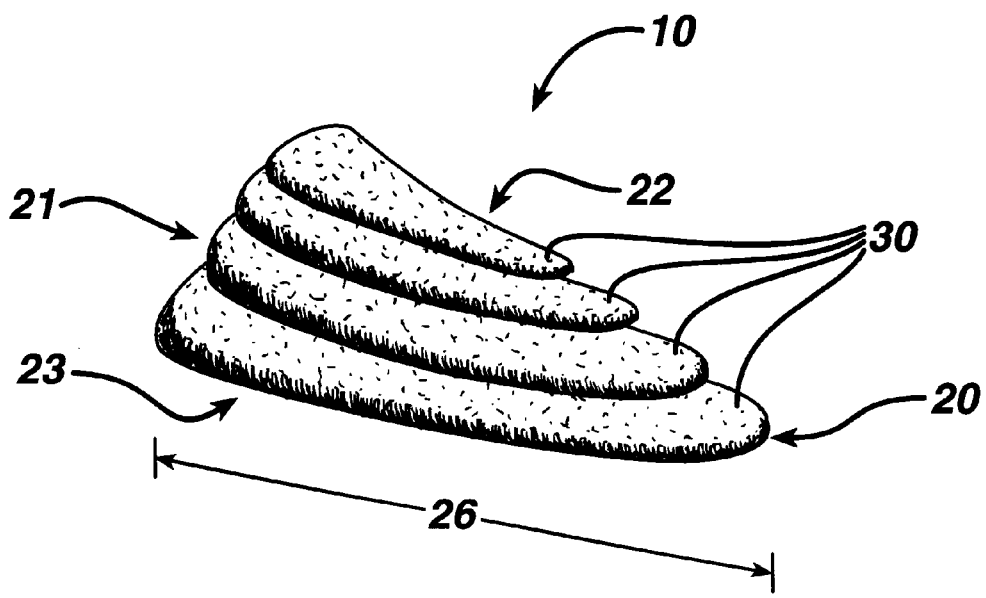
FIG. 1 is a perspective view of an article according to the invention.
Figure 2:
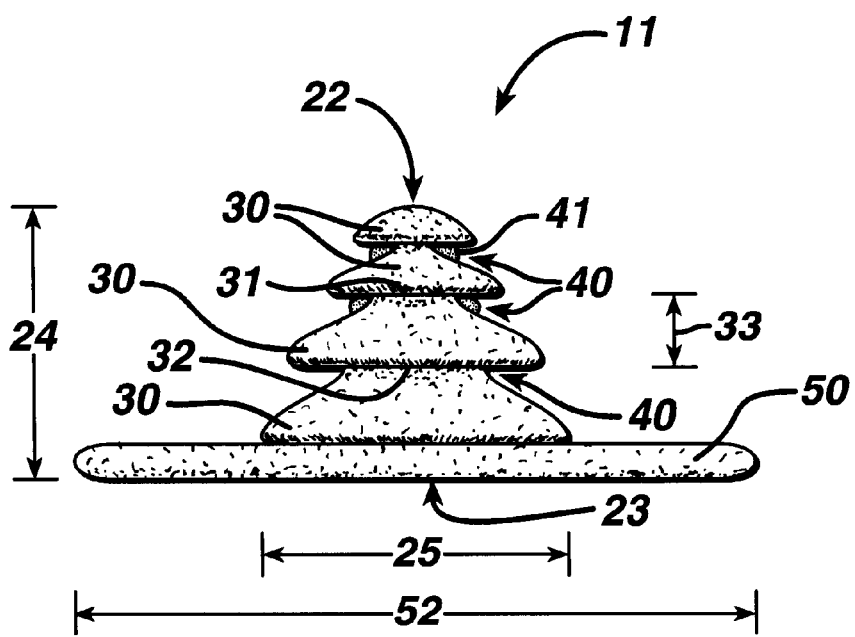
FIG. 2 is an end view of an alternative embodiment of an article according to the invention comprising a base member and channels between adjacent flexible elements.

FIG. 1 is a perspective view of one embodiment of the interlabial article, while FIG. 2 is an anterior end view of an alternative embodiment. Interlabial articles 10 and 11 each comprise an anterior end 20 that faces the clitoris in use; a posterior end 21 that faces the posterior fourchette; a body-facing side 22 that penetrates the labia; and an opposing side 23. The height 24, width 25 and length 26 of the articles are also shown in FIGS. 1 and 2.

The interlabial article comprises a plurality of stacked, flexible elements 30. Each flexible element has a top 31 proximal the body-facing side 22 of the article, a bottom 32 proximal the opposing side 23 of the article, and a thickness 33. The flexible elements 30 of the article are stacked one on top of another from the opposing side 23 to the body-facing side 22 of the article. The shape and size of the flexible elements may vary; however, it is preferred that they increase in size from the body-facing side 22 to the opposing side 23 of the article, as depicted in the Figures.

The perimeters of successive, horizontal cross-sections of each flexible element 30 can be substantially the same, increase, or decrease from the top 31 to the bottom 32 of the flexible element. When the perimeters of successive, horizontal cross-sections of each flexible element 30 vary, channels 40 are defined between adjacent flexible elements. Preferably, the perimeters of successive, horizontal cross-sections of each flexible element 30 increase from top to bottom of the flexible element 30, thereby directing the channels 40 towards the opposing side 23 of the article. In this embodiment of the invention, shown in FIGS. 1 and 2, the article is substantially easier to insert than remove. This is because the flexible elements 30 have a tendency to flare out against adjacent body tissue when the article is pulled directly away from the labia, thereby increasing the friction during the dynamic state of removing the article. Also, tissue in the perineum area can potentially reside, or be caused to reside, between the flexible elements during or prior to removal, thereby increasing frictional forces on removal of the article.

Figure 3:
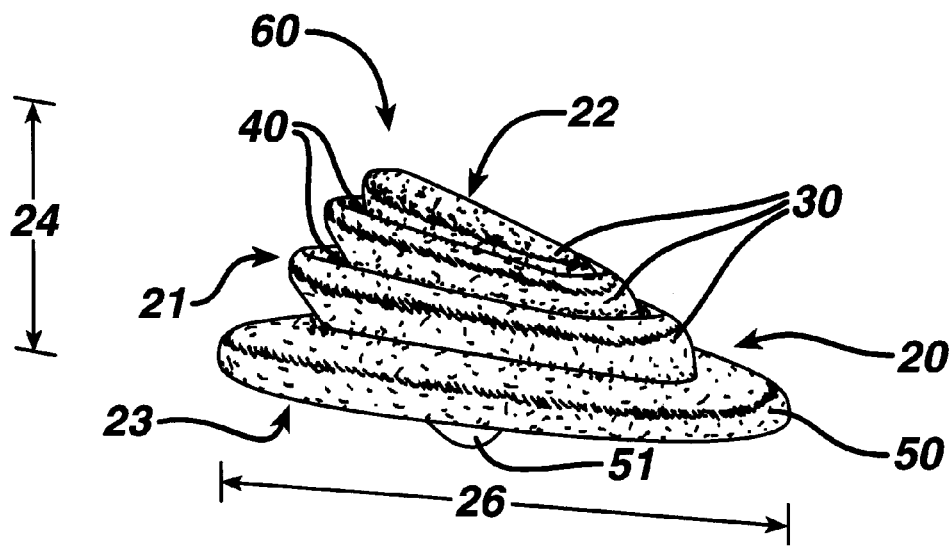
FIG. 3 is a perspective view of a further article according to the invention, comprising a base member, an insertion aid and channels between adjacent flexible elements.
Figure 4:
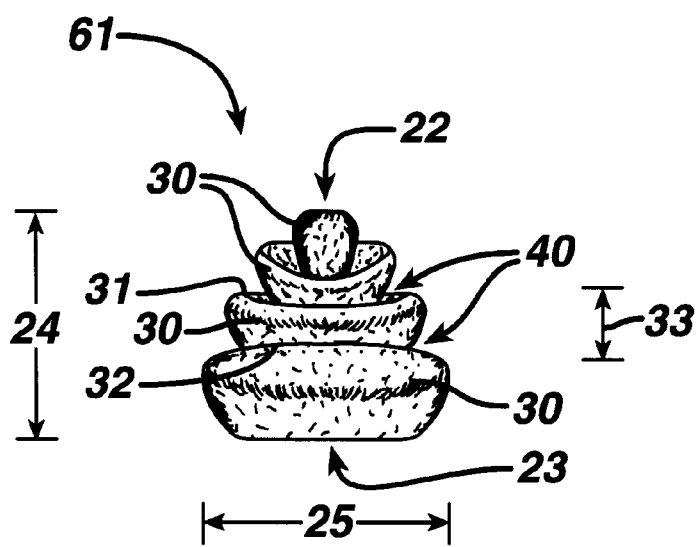
FIG. 4 is an anterior end view of an article according to the invention comprising channels directed towards the body-facing side of the article.

In an alternative embodiment, the perimeters of successive, horizontal cross-sections of each flexible element 30 decrease from top to bottom of the flexible element 30, thereby forming channels 40 directed towards from the body-facing side 22 of the article. This is illustrated in FIGS. 3 and 4. Body-facing channels can provide a means for collecting and maintaining bodily fluids not directly absorbed into the article, such as viscous fluid, sloughed tissue conglomerates, blood constituents, and combinations thereof. Conveniently, on removal of the article, the flexible elements bend to close the channel and retain any captured material for a clean removal and disposal. Flexible elements with body-facing channels offer the further potential benefit of obtaining and securing samples of tissue or discharged fluids for diagnostics. Insofar as the flexible elements flex outwardly and open during insertion, they gently scrape the body, and then close during removal, capturing any obtained sample material.

The number of flexible elements 30 useful in the article is at least 2, preferably from 2 to 8, more preferably from 3 to 5. Each flexible element thickness 33 is preferably from about 0.5 to about 10 millimeters, more preferably from about 1 to about 6 millimeters.

FIG. 1 further depicts optional base member 50, having a width 52, on the opposing side 23 of the article. The base member can reside either intralabially or extralabially. The base member can also be sized and configured for wrapping around, and attaching to, the crotch portion of a user's undergarment. The width of the optional base member 52 is preferably from about 20 to about 80 millimeters, more preferably from about 30 to about 60 millimeters.

Article height 24 should be sufficient to permit penetration of the space between the labia to capture and absorb liquid discharges from the body, without placing excessive pressure on the labia minora and the vestibule. Article height 24 is preferably from about 5 to about 40 millimeters, more preferably from about 15 to about 25 millimeters. The article height 24 may be constant along the length 26 of the article. Alternatively, the article height 24 can vary along the length 26 of the article to provide optimum comfort and fluid management. The article height 24 is, for example, preferably higher at the posterior end 21 of the article, to capture vaginal discharges, than at anterior end 20, where it preferably does not encroach on the sensitive clitoris. The article height 24 may be the same or different at the anterior and posterior ends 21 and 20 of the article, while the same, a higher, or a lower height in between.

The length 26 of the article may range from about 25 to about 130 millimeters, preferably from about 30 to about 80 millimeters, more preferably from about 40 to about 60 millimeters, depending on such factors as whether the article is intended to cover the vaginal orifice, the urethral meatus, or both (without irritating the clitoris and posterior fourchette), and the anatomical dimensions of the user. Some consumers may desire the article to cover both the vaginal opening and the urethral meatus for management of both cervical discharges and urine. Alternatively, an interlabial article with a reduced length 26 enables the article to remain in place for collecting vaginal discharge, while allowing unrestricted urination.

The article width 25 preferably varies in the range of about 8 to about 40 millimeters, more preferably about 10 to about 20 millimeters. The width 25 may vary or be constant along the length of the article FIG. 2 further depicts an optional additive 41. Additive 41 is shown as discrete applications positioned in the channels 40 defined by the three flexible elements 30 most proximal the body-facing side 22 of the article. Additive 41 can alternatively be placed as a coating on the surface of one or more flexible elements 30. A representative, nonlimiting list of additives includes medicaments, moisturizers, vitamins and minerals, spermicides, and odor controlling agents. A single additive can be employed or multiple additives providing different functions can be employed.

Odor controlling agents useful as additives are described in greater detail in U.S. Pat. Nos. 4,356,190; 4,273,786; 5,306,487; 5,733,272; 5,714,445 and 5,211,870.

Examples of useful medicaments providing bacterial-treating properties are described in U.S. Pat. Nos. 5,811,115; 5,514,698; 5,837,254; 5,466,463; 5,573,765; 5,536,743; 5,314,904; 5,141,953 and 5,679,369. Medicaments for treating abnormalities of the tissues and organs in the perineum, such as vulvar dystrophy, vaginal atrophy and vaginal mycoses, are described in U.S. Pat. Nos. 5,380,757; 5,352, 699; and 4,582,717.

U.S. Pat. No. 5,015,474 describes moisturizers for dermal or mucosal membranes. The article of the present invention provides a vehicle for administering such compositions, due to the intimate contact with the labia and vaginal entroitus.

FIG. 3 depicts an optional insertion aid 51 extending from the opposing side 23 of the article. The insertion aid 51 can be grasped either by a user's fingers, or used with an applicator such as those used to insert commercial tampons or a modification thereof A further embodiment of the article comprises core elements positioned between adjacent flexible elements, wherein each flexible element extends laterally away from the core elements, thereby forming channels between adjacent flexible elements. FIGS. 5 and 6 illustrate absorbent interlabial articles 70 and 71 comprising four flexible elements 30, three core elements 81 positioned between the flexible elements 30, and channels 40. An optional insertion aid 51 is also depicted in FIG. 6.

A vertical cross-section of FIG. 5 along line A—A is shown in FIG. 6. The flexible elements 30 of FIG. 6 have generally trapezoidal vertical cross-sections. However, the flexible elements may have other cross-sectional shapes, such as rectangular, circular, or triangular. The core elements 81 preferably have a height 34 of about 1 to about 4 millimeters. The flexible elements 30 of FIG. 6 have a thickness 33 that is greater at locations distal the core elements 81 compared to locations proximal the core elements 81. This thickness differential provides improved retention of adsorbed or absorbed fluids and liquids, or additives. The thickness 33 may be uniform as shown in FIG. 7.

The flexible elements 30 extend from the core elements 81 at substantially right angles (90 degrees) in FIGS. 5 and 6. The flexible elements may, however, extend at angles of less than 90 degrees as measured from core elements proximal the opposing side of the article.

The interlabial article can be formed as a single unit, such as in a foam molding operation, or the flexible elements can be manufactured individually and then attached to one another, such as by the use of adhesives, heat sealing with thermoplastic materials, hook and fastener technology, and ultrasonics. In the case of foam molding, by manipulating the foam material and/or molding process, both open celled and closed celled surfaces may be formed. Open celled surfaces are useful for absorbing bodily fluids, while closed celled surfaces can act as a barrier to prevent captured fluid from travelling completely through the article and onto a user's skin or clothing.

Additional methods and apparatuses useful in forming the articles of the present invention as a single structure are described in U.S. Pat. Nos. 5,165,152; 4,863,450; 4,859,273; 4,816,100; and 4,453,296. These methods generally consist of folding or rolling a web comprising fibrous materials onto itself into a blank, and then compressing the blank into a final form with heat and pressure. The blank typically takes a desired final form due to either the flowing and resetting of thermoplastic polymers in the web, or by the web being plastically deformed (non-recoverable deformation) sufficiently.

A useful web for this purpose is a single nonwoven web comprising blends of bicomponent thermoplastic fibers, such as polyethylene/polyester sheath core fibers, woodpulp, and superabsorbent polymers. The web may comprise several layers with the outer layers void of any absorbent material (i.e., woodpulp and superabsorbent polymer).

A fibrous web or film may be folded or pleated into the final interlabial article without an extra compression step as described above. Construction adhesives known in the art may be optionally employed to aid in keeping the folds or pleats in their desired final form, or alternatively to adhere separately made flexible elements of the article together. A representative, non-limiting list of construction adhesives includes acrylics; starch based hot melts; adhesives based on block copolymers of vinyl aromatic hydrocarbon and one or more conjugated diene or hydrogenated aliphatic blocks; polylactic acids; hot melts based on polyolefins such as amorphous polyalphaolefins that may consist of one or more of the following monomers: propylene, ethylene, butane, and hexene; hot melts based on low density polyethylene or low density polyethylene copolymers including ethylene vinyl acetate, methyl acrylate, n-butyl acrylate, and acrylic acid.

Conventional methods used in constructing articles for managing bodily-fluids, such as sanitary napkins, pantiliners, and ultrathin napkins may also be used to make the interlabial article. These methods typically bond or encase multiple material layers or particulates together. The material layers or particulates may be in the form of apertured or non-apertured polymeric films, foam sheets, fibrous webs, superabsorbent fibers and/or particles, and woodpulp.

The absorbent material used in the interlabial article may comprise either simple or complex absorbent structures that accept, transfer, distribute, store, or retain fluid as well as prevent fluid from exiting the article. The absorbent material may be composed of one or more layers of like or dislike components. The absorbent material may be a simple absorbent such as woodpulp, which in turn may contain stabilizing components such as synthetic fibers. The absorbent material may be uncompressed, compressed, or otherwise densified, at least in part. Compression and densification may be homogeneous throughout the absorbent material or in discrete layers or in continuous or discontinuous gradients of density.

Synthetic fibers in the absorbent material may be employed to form a bridging matrix within the wood pulp, or may be thermobonded and fused to themselves and to the woodpulp to form a dimension stabilizing structure. The synthetic fibers may also be either hydrophilic, such as rayon, or hydrophobic, such as polypropylene or polyester. The synthetic fibers may be made more wettable by treatment with a wetting agent such as a surfactant, by caustic etching of the fibers such as those made of polyester, by incorporating wettable polymers such as polyethylene oxide or polyvinyl alcohol, by grafting wettable reactants to the fiber surface and by exposing the fiber to corona discharge. The peripheral profile of synthetic fibers may be of any shape. The synthetic fibers may also contain grooves, channels, or bores, and may be pitted or perforated.

Superabsorbent polymers may also be employed in or as the absorbent material to increase the liquid management properties of the articles, such as capacity and retention of fluids. The amount of superabsorbent polymer contained by the article can range from about 0.1 to about 5 grams, preferably from about 0.2 to about 2.5 grams, more preferably from about 0.3 to about 1 grams.

Absorbent materials such as sphagnum moss, in board or in compressed layer form, may additionally function as compression or deformation resisting structures or to help maintain the shape of the article in production and in use. Absorbent materials in board form may be made flexible and conforming by tenderizing, such as passing the board through corrugating, embossing or perforating processes.

Woodpulp may be at least in part comprised of any of wet crosslinked, dry crosslinked, chemically stiffened or curly fibers. The synthetic fibers and auxiliary absorbents may be present homogeneously throughout the absorbent material, in discrete layers or in continuous or discontinuous concentration gradients. The absorbent material may also contain foam in the form of layers or particles, the foam being either hydrophobic or hydrophilic, depending on its place and function in the product, e.g., absorbing, cushioning, deformation resisting and compression resisting.

A liquid permeable cover may optionally be used to encase portions of the absorbent material. The liquid permeable cover may be made of at least one layer of any material penetrable by liquids, including woven or knitted fabrics, but preferably a onwoven fabric, non-reticulated open cell foam, perforate film or combinations thereof. Nonwoven fabrics include any of those made of staple fibers or continuous filaments. The nonwoven fabrics can employ natural fibers such as cotton, jute, ramie, woodpulp or kenaf. The nonwoven fabrics can alternatively comprise synthetic fibers, alone or in combination with natural fibers. A representative, non-limiting list of synthetic fibers includes rayon, polyolefins such as polyethylene, polypropylene, polyesters, polyamides, polyacrylonitriles, polyvinyl esters and multicomponent fibers, the multicomponent fibers being made of a low melting polymer that is at least in part exposed on the fiber's surface and a high melting polymer. The nonwoven fabrics may be created from the fibers and/or filaments by any of the known fabric forming processes, where applicable, such as web consolidation and bonding processes, e.g., by wetlaying or drylaying fabrics bonded with chemical binders or by thermal means such as through-air bonding, or by direct fabric forming processes, e.g., by hydroentangling, spunbonding or meltblowing.

Perforate films useful in the liquid permeable cover have perforations that may be of two or three dimensions in profile through the thickness of the film, the films being made of polymers that include polyethylene, polypropylene, polyurethane, polyamide, copolymers of ethylene and vinyl acetate and the like and combinations thereof.

The fabrics or perforate films employed in the liquid permeable cover may be made wettable to varying degrees, e.g., by treatment with a surfactant, by exposure to corona discharge, by grafting the film with wettable reactants, by caustic etching of films such as those made of polyester, or by incorporating wettable polymers such as polypropylene oxide and polyvinyl alcohol in the polymeric formulation used to make the fibers or films.

In an effort to improve the fluid management properties of the absorbent interlabial article, an optional transfer layer can be added, typically between the absorbent material and the liquid permeable cover. However, the transfer layer may be located elsewhere, e.g., within or below the absorbent material. Transfer layers can provide many functions including but not limited to wicking fluid to available absorbent material, acting as a one-way valve to prevent captured fluid from squeezing out, and providing resiliency to the article to prevent it from collapsing, especially when occupied with fluids.

Transfer layers typically comprise relatively less hydrophilic materials and structures than those contained in the absorbent material, such as webs of meltblown polypropylene or polyester fibers. Transfer layers may also contain woodpulp, cotton, or rayon entrained within. The transfer layer may also be comprised of low density, highloft nonwoven webs comprised of woodpulp and synthetic fibers such as polyethylene, polypropylene, polyester, polyacrylonitrile and polyamide and multicomponent fibers described above. Such highloft nonwoven webs may be bonded with chemical binders or by thermal means such as through-air bonding and thermal embossing. The transfer layer may also comprise a perforate film, whose profile through the thickness of the film is either two-dimensional or preferably three-dimensional.

Multiple transfer layers may also be employed as a means for improving the article's ability to manage fluid and for providing structurally stability. U.S. Pat. No. 5,752,945 discloses an absorbent article having a transfer sheet, wherein the transfer sheet has at least two layers. The first layer can provide wet and dry resilience and liquid holding capacity, while the second layer can provide lateral wicking or flow paths in order to distribute liquid across an absorbent core more uniformly.

The interlabial article may comprise additional materials to encase portions of the absorbent material. In particular, the opposing side of the article can be covered at least in part with a liquid impermeable backsheet to help prevent the captured fluid from transferring to a user's body and/or clothing. The liquid impermeable backsheet may also contain portions of adhesive on its outwardly disposed surface, whereby a user can optionally attach the article to her undergarment. The liquid impermeable backsheet can be of any flexible material that prevents the transfer of liquid through it but does not necessarily prevent the passages of gases. Commonly used materials are polyethylene or polypropylene films. Other materials that may be used as the liquid impermeable backsheet are films of polyesters, polyamides, ethylene vinyl acetate, polyvinyl chloride, polyvinylidene chloride, cellophane, nitrocellulose and cellulose acetate. Coextruded and laminated combinations of the foregoing, wherein such combinations are permitted by the chemical and physical properties of the film, may be used. Liquid impermeable reticulated foams and repellent treated papers may also be used.

Films that are barriers to liquids but do permit gases to transpire, i.e., "breathable barriers," may also be used as the liquid impermeable backsheet. These may be selected from polyurethane films and from microporous films in which microporosity is created by ionizing radiation or by leaching out of soluble inclusions using aqueous or nonaqueous solvents. Single or multiple layers of permeable films, fabrics and combinations thereof, that provide a tortuous path, and/or whose surface characteristics provide a liquid surface repellent to the penetration of liquids may also be used to provide such breathable barriers.

The materials used to make the absorbent material, liquid permeable cover, liquid impermeable backsheet, and transfer layer above can be water soluble or dispersible and/or biodegradable, in an effort to provide a more flushable or less environmentally persistent article. A non-limiting, representative list of such materials includes polyvinyl alcohol, polylactic acid, starch and starch based formulations, polyhydroxybutyrate, and combinations thereof. The materials can also have extensible or stretchable properties by performing a mechanical operation, such as pleating, corrugating, or ring rolling on them. In addition, the materials can be perforated or slit. The perforations or slits can vary in geometry and size, thereby providing extensibility in multiple directions if needed. The materials can also be inherently stretchable, such as polyethylene blended films available from Exxon, particularly film EXX-7. A more detailed disclosure of extensible articles, and methods of making them, is contained in U.S. Pat. No. 5,824,004.

An example of an absorbent interlabial article of the present invention constructed from multiple layers of material is depicted in FIG. 7. Cross-section 70 depicts a liquid permeable cover 91, a transfer layer 92 underneath the liquid permeable cover, and a liquid impermeable backsheet 93 overlaying the opposing side 23 of the article. The liquid permeable cover 91 and the transfer layer 92 are shown partially covering the body-facing side 22 of the article. Alternatively, these layers may cover substantially the entire body-facing side of the article.

The dimensions and material properties of the flexible elements 30 are preferably selected such that the amount of force required to overcome the friction between the user's body and the article is greater than the force required to bend the elements. Given The various natural moisture levels in the body and the variety in saturation and distortion levels of the article, the flexible elements may or may not flare (inwardly or outwardly) substantially during insertion or removal of the article. However, the peak force required to displace an individual flexible element through a maximum angle of 90 degrees is preferably from about 10 to about 130 grams force using the following test method.

A Model 1122 Instron testing instrument, available from Instron Corporation, Canton, Mass. is used in concert with a 2,000-gram load cell. A pin, having a diameter of 1.58 millimeters, is rigidly connected to the load cell. The cross head, housing the load cell and pin, is displaced at a speed of approximately 17 millimeters per second. The article is mounted on an adjustable plate, allowing for multiple measurements at various points on a single article. The pin contacts a flexible element at a point sufficiently distal its longitudinal centerline, allowing the pin to remain in contact with the flexible element through the entire 90 degrees rotation without slipping off. Test conditions are approximately 73° F. and 58% relative humidity. The peak force required to independently (without contacting adjacent flexible elements) displace each of the flexible elements through a maximum angle of 90 degrees is measured. The values are reported in gram force. The samples are not necessarily conditioned at TAPPI standard conditions.

The article of the present invention is intended to be worn independently substantially within the labia minora and majora. The article may also be worn in conjunction with other available fluid management products, such as tampons, intravaginal cups, sanitary napkins, and the like. The article may also be modified to be coupled, such as with adhesives or hook and loop fastening systems, with the products described above, and inserted and removed together. Additionally, the article may be commercially sold as part of a kit. The complementary parts of such a kit might include wipes, applicators for inserting the articles, moisturizers, and other fluid management products. Lastly, the article may be configured and sold in individual wrappers. Examples of individually wrapped products are described in greater detail in U.S. Pat. Nos. 4,556,146 and 5,462,166.

The disclosures of all patents, as well as any corresponding published foreign patent applications, mentioned throughout this patent application are hereby incorporated by reference.

EXAMPLE

An interlabial article of the invention was made as follows.

Hypol 2002 prepolymers (polyether polyurethanes), commercially available from Hampshire Chemical Corporation, Lexington, Mass., were mixed in a 1:1 volumetric ratio with an aqueous phase containing deionized water and 0.5% Tween 20 surfactant (commercially available from ICI), then poured into a prefabricated rubber mold to yield a foam interlabial article with hydrophilic properties. The article comprised three flexible elements for interlabial application, a base member, and an insertion aid. The base member had an overall length of 64 mm, an overall width of 39 mm, and a thickness of 4.4 mm. The insertion aid had a length of 15 mm, a width of 3.7 mm, and a height of 6 mm. The three flexible elements had the following dimensions:

Lower element: Length: 50 mm Width: 17 mm Height (anterior): 3.5 mm Height (posterior): 7 mm Middle element: Length: 39 mm Width: 12 mm Height (anterior): 6.5 mm Height (posterior): 11.5 mm Top element: Length: 30 mm Width: 6 mm Height (anterior): 9 mm Height (posterior): 14.5 mm Height measurements were taken from the opposing side of the article to the top of each element, not including the thickness of the base member.

The article was then laminated to a nonwoven liquid-repellent backsheet (19 gsm spunbonded polypropylene, 0.2 mm thickness, hydrophobicity 25 mm $H_2O$ using EDANA 180.20 test method, commercially available from PGI Nonwovens). Laminating adhesive from HB Fuller Company designated 1491 XZP was used to adhere the backsheet to the opposing side of the article. Excess backsheet was trimmed so that the backsheet was shaped to the base of the article, producing an interlabial article of hydrophilic foam adsorbent comprising flexible elements and a base member, and a hydrophobic nonwoven backsheet attached thereto.

The peak force required to displace an individual flexible element of the interlabial article through a maximum angle of 90 degrees was measured employing the test method described above using a Model 1122 Instron testing instrument. Test conditions were at 73 degrees F and 58% relative humidity. Measurements were taken at three locations on each flexible element: one at the posterior end and one at each side, using the midpoints along the length of the flexible element. The peak force for the lower flexible element ranged from 20.7 g to 81.8 g at a 0.15 inch to 0.35 inch distance of travel by the pin gauge. The peak force for the middle flexible element ranged from 21.8 g to 86.6 g at a 0.4 inch to 0.55 inch distance of travel. The peak force for the topmost element ranged from 42.2 g to 88.7 g at a 0.9 inch to 1.0 inch distance of travel.

What is claimed is:

1. An absorbent interlabial article sized and configured to fit between a user's labia, said absorbent interlabial article having a body-facing side, an opposing side, and an interlabial portion, wherein the interlabial portion comprises a plurality of stacked, flexible elements, at least one of the flexible elements comprises absorbent material, and core elements positioned between adjacent flexible elements, wherein each flexible element extends laterally away from the core elements, thereby forming channels in the regions between adjacent flexible elements.

2. The article of claim 1 wherein each core element has a height of about 1 to about 4 millimeters.

3. The article of claim 1 wherein each flexible element has a thickness that is greater distal the core elements than proximal the core elements.

* * * * *